United States Patent [19]

Beyer et al.

[11] Patent Number: 4,775,005
[45] Date of Patent: Oct. 4, 1988

[54] METHOD AND DEVICE FOR THE PROTECTION OF STEAM GENERATORS, ESPECIALLY NUCLEAR REACTOR STEAM GENERATORS

[75] Inventors: Werner Beyer, Erlangen; Norbert Wieling, Igensdorf; Bernhard Stellwag, Nuremberg, all of Fed. Rep. of Germany

[73] Assignee: Kraftwerk Union Aktiengesellschaft, Mülheim, Fed. Rep. of Germany

[21] Appl. No.: 828,280

[22] Filed: Feb. 11, 1986

[30] Foreign Application Priority Data

Feb. 13, 1985 [DE] Fed. Rep. of Germany ....... 3504925

[51] Int. Cl.$^4$ .................. G05D 21/00; F22B 37/42; G21C 17/00; G21D 3/08
[52] U.S. Cl. ................. 165/134.1; 204/404; 376/306
[58] Field of Search ............. 165/11.1, 134.1; 376/305, 306, 328; 204/1 T, 1 C, 404

[56] References Cited

U.S. PATENT DOCUMENTS

| | | | |
|---|---|---|---|
| 3,520,790 | 7/1970 | Araki et al. | 165/134.1 |
| 3,624,241 | 11/1971 | Power | 376/328 |
| 3,880,226 | 4/1975 | Houser et al. | 165/11.1 |
| 4,338,959 | 7/1982 | Krueger et al. | 165/11.1 |
| 4,586,562 | 5/1986 | Carlson et al. | 165/134.1 |
| 4,588,022 | 5/1986 | Sanz | 165/134.1 |
| 4,636,292 | 1/1987 | Fejes et al. | 204/404 |

OTHER PUBLICATIONS

Corrosion Science, 1970, vol. 10, No. 12, p. 885, Pergamon Press.
Jacob et al., Materials Performance, Apr., 1977, pp. 9-14.
Bignold, Nuclear Engineering International, Jun. 1981, pp. 37-41.
Journal "Kernenergie" (Nuclear Energy), vol. 27, No. 4, p. 156, 1984.

Primary Examiner—Deborah L. Kyle
Assistant Examiner—Richard W. Wendtland
Attorney, Agent, or Firm—Herbert L. Lerner; Laurence A. Greenberg

[57] ABSTRACT

A method for the corrosion protection of steam generators having a housing containing feed water and enclosing a tube bundle with tubes conducting a heat carrier includes continuously determining the redox potential of the feed water during operation of the steam generator, continuously determining the corrosion potential of at least one tube of the tube bundle during operation of the steam generator, and negatively shifting the redox and corrosion potentials by changing the chemical conditioning of the feed water if the potentials indicate the danger of corrosion, and a device for carrying out the method.

18 Claims, 2 Drawing Sheets

METHOD AND DEVICE FOR THE PROTECTION OF STEAM GENERATORS, ESPECIALLY NUCLEAR REACTOR STEAM GENERATORS

The invention relates to a method for the protection of steam generators against corrosion by chemically conditioning the feed water, the steam generator having a housing containing feed water and enclosing a tube bundle which conducts a heat carrier. The invention also relates to a device particularly well suited for carrying out the method, which has particular significance for nuclear reactors.

It is known from the article "Elektroden füor Elektrochemische Messungen in Druckwassersystemen" (Electrodes for Electrochemical Measurements in Pressurized-Water Systems) in the journal "Kernenergie" (Nuclear Energy), Vol. 27, No. 4, especially page 156, that ferrous materials such as are used in the construction of steam generators, usually suffer no corrosion in highly pure water that is free of oxygen. However, this changes with rising temperatures. Therefore, there are various chemical feed water conditioning measures used in steam generating to prevent or at least to reduce corrosion.

In the above-mentioned article in the "Kernenergie" journal, a special electrode configuration is used to determine the redox potential and to determine the variation in time thereof in the reactor loop of a pressurized-water system; this configuration is also to determine the rest potential of exposed material samples which is correlated with the corrosion susceptibility.

These and other measurements are said to be significant for the clarification of corrosion processes and for the development of corrosion protection measures. Therefore, more calculations, investigations, etc. are needed before the corrosion protection of a pressurized-water system is actually improved.

It is accordingly an object of the invention to provide a method and device for the protection of steam generators, especially nuclear reactor steam generators, which overcomes the hereinafore-mentioned disadvantages of the heretofore-known devices of this general type, and which directly improves the corrosion protection on the secondary side of steam generators of the above-mentioned kind. In contrast to the prior art, according to the invention further scientific investigation or laboratory work is to be dispensed with.

With the foregoing and other objects in view there is provided, in accordance with the invention, a method for the corrosion protection of steam generators, especially of nuclear reactors, having a housing containing feed water and enclosing a tube bundle with tubes conducting a heat carrier, which comprises continuously determining the redox potential of the feed water during operation of the steam generator, continuously determining the corrosion potential of at least one tube of the tube bundle during operation of the steam generator, and negatively shifting the values of the redox and corrosion potentials by changing the chemical conditioning of the feed water if the potentials indicate the danger of corrosion.

The invention thus results in an electrochemical measurement conducted during operation, by means of which endangerment of the steam generator tube system by corrosion can be detected and eliminated at the earliest possible moment. The corrosion potential of the steam generator tube system determined in accordance with the invention gives information as to how the tubes react to variations in the water chemistry indicated by the redox potential. This makes it possible to initiate countermeasures before damage can occur.

In accordance with another feature of the invention, there is provided a method which comprises adding conditioning substances dissolved in liquid to the feed water by remote control. The conditioning, in particular the changing of the conditioning on the basis of the potential measurements, is advantageously accomplished in this manner because this accomplishes both the dosing and the necessary distribution in the feed water in a particularly favorable manner.

In accordance with a further feature of the invention, there is provided a method which comprises presetting the quantity of the conditioning substances with a timing control circuit. This provides an even liquid flow by means of the control circuit. However, it is also possible to dose by means of small individual quantities added to the feed water in a clocked and countable manner.

In accordance with an added feature of the invention, there is provided a method which comprises measuring the redox potential in a lower region of the tube bundle relative to an external reference electrode being inert relative to the feed water.

In accordance with an additional feature of the invention, there is provided a method which comprises measuring the redox potential in the vicinity of a tube sheet at the bottom of the tube bundle.

Sludge in which corrosion-promoting ions (e.g. chlorides, sulfates) concentrate over the long term can deposit in this area. These ions lead to a pronounced shift of the specified steam generator water quality in the direction of concentrated, aggressive solutions. This can be detected and stopped by practicing the invention.

In accordance with again another feature of the invention, there is provided a method which comprises electrolytically connecting a reference electrode outside the steam generator to a tube with an electrolyte key, and measuring the corrosion potential of a tube by measuring the voltage of the reference electrode relative to the housing or a tube sheet supporting the tubes having a d-c or galvanic connection to the tube.

The continuous potential determination during the operation of the steam generator which is characteristic of the invention, requires functionally reliable and failproof devices which must be capable of withstanding high pressures and temperatures.

In order to provide such a device, there is provided, in accordance with the invention, a device for protecting steam generators against corrosion, comprising a housing containing feed water to be chemically conditioned, a tube bundle disposed in the housing, the tube bundle including tubes conducting a heat carrier and having a d-c or galvanic connection to the housing, a reference electrode disposed outside the steam generator, an electrolyte key electrolytically connecting the reference electrode to one of the tubes, and means for measuring the corrosion potential of the one tube by measuring the voltage of the reference electrode relative to the housing, the electrolyte key being a small, mechanically strong tube with an outer metal jacket, an insulating inner metal oxide coating, a thermoplastic hose disposed inside the coating, and a fiber core disposed inside the hose. The voltage of the reference electrode may also be measured relative to a tube sheet having d-c or galvanic connection to the tube.

In accordance with again a further feature of the invention, the metal jacket is formed of a material from the group consisting of zirconium, titanium, tantalum, hafnium and corrosion-resistant CrNi steel.

In accordance with again an added feature of the invention, the fiber core is formed of asbestos and the hose is formed of polytetrafluorethylene.

In accordance with again an additional feature of the invention, the reference electrode is a second type or order electrode preferably formed of silver/silver chloride and is enclosed in a metal electrode housing.

In accordance with a concomitant feature of the invention, the electrode housing has a threaded nipple enclosing the electrolyte key and being fastened to the steam generator by the electrolyte key.

Other features which are considered as characteristic for the invention are set forth in the appended claims.

Although the invention is illustrated and described herein as embodied in a method and device for the protection of steam generators, especially nuclear reactor steam generators, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
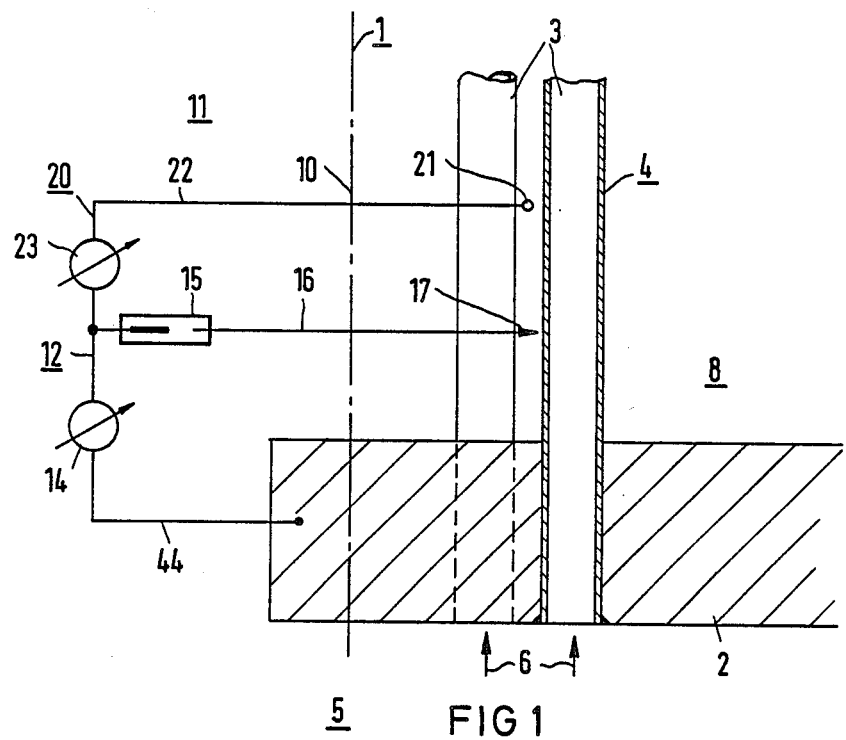
FIG. 1 is a fragmentary, diagrammatic, cross-sectional view of a steam generator and a basic schematic circuit diagram of a device for protecting the steam generator according to the invention.

Referring now to the figures of the drawings in detail and first, particularly to FIG. 1 thereof, there is seen a fragmentary illustration of a steam generator of a pressurized-water power reactor including a tube sheet 2. The tube sheet is a steel plate in which the ends of tubes 3 of a tube bundle 4 are embedded. The tubes 3 may be formed of Incoloy 800 and are heated by the primary water of the pressurized-water reactor entering the tubes 3 from a primary chamber 5 below the tube sheet 2 in the direction of arrows 6. A secondary space 8 above the tube sheet 2 contains feed water which is to be evaporated by the heat of the tubes 3. The evaporation pressure is approximately 70 bar and the steam temperature is approximately 290° C. The primary water is hotter, its temperature being over 300° C. and the pressure in the primary chamber 5 being 160 bar or more. This results in great stresses on the tube bundle 4, the tube sheet 2 and the housing wall of the steam generator 1 which is indicated by a straight dot-dash line 10 forming a separation between the interior of the steam generator 1 and the surroundings 11.

A measuring circuit 12 for measuring the electrode potential is connected to the tube sheet 2 by a silver wire 44. The circuit 12 includes a millivoltmeter 14, a reference electrode 15 and an electrolyte key 16 passing through the wall 10 of the steam generator 1 and having a tip 17 in the vicinity of the lower region of the steam generator tube 3 near the tube sheet. The distance from the tip 17 of the electrolyte key 16 to the tube sheet is only about 2 to 5 times the tube diameter.

Another measuring circuit 20 picks up the radox potential. The circuit 20 includes another electrode 21 which is preferably formed of platinum and is disposed near the tip 17 of the electrolyte key 16. The electrode 21 is connected to the reference electrode 15 by an insulated electric wire 22 passing through a millivoltmeter 23.

Figure 2:
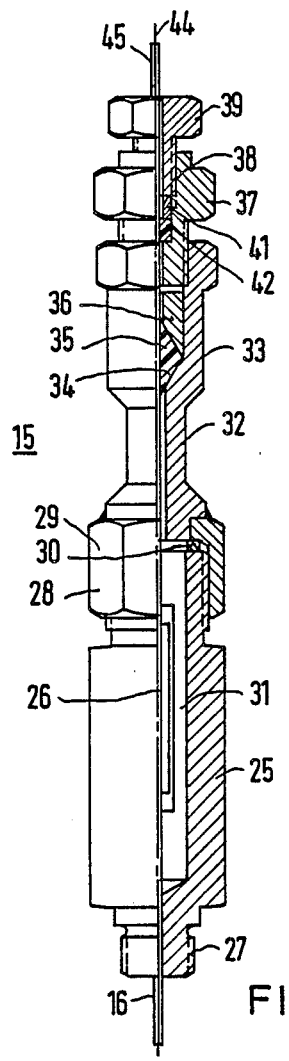
FIG. 2 is a view of a device for the execution of the method according to the invention, the left side of the figure illustrating an elevational view of the outer contour thereof and the right side of the figure illustrating a longitudinal-sectional view thereof.

FIG. 2 shows the construction of the reference electrode 15. It may be seen that a hollow cylindrical metal housing 25 encloses a central electrode configuration 26 with a suitable second order electrode, e.g. with silver/silver chloride components. The lower end of the metal housing 25 in FIG. 2 has a threaded nipple 27. The nipple 27 is used to screw the metal housing 25 into the wall 10 of the steam generator 1. A cover 29 having similar to a nut a hexagonal surface 28 is screwed to the end of the metal housing 25 opposite the threaded nipple 27. The cover 29 presses a seal 30 between the cover 29 and the housing 25 so that the interior 31 of the reference electrode 15 is sealed in a pressure-tight and temperature-stable manner according to the construction data of the steam generator 1.

The cover 29 extends upwardly in the form of a cylindrical extension 32 which becomes an expansion 33. The expansion 33 encloses a double-conical inner chamber 34 into which a double-conical Teflon seal 35 is inserted. The seal 35 is placed under pressure by a hollow tapered cap 36 which is pressed by a clamping tube 37 which in turn forms a tapped hole 38 to accomodate a clamping screw 39. When the clamping screw 39 is screwed into the clamping tube 37 it compresses a Teflon ring 42 by means of a metal ring 41. This provides a double seal for the silver wire 44 which is enclosed in a Teflon hose 45 and is thus insulated. The silver wire 44 forms a d-c or galvanic connection to the tube sheet 2 across the millivoltmeter 14 shown in FIG. 1. The wire 44 is also connected to the millivoltmeter 23.

Figure 3:
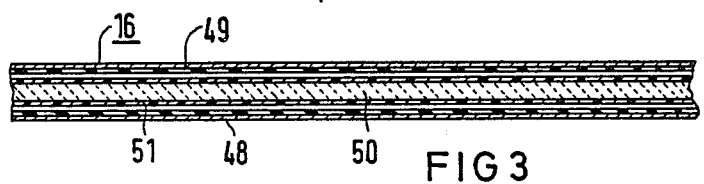
FIG. 3 is a cross-sectional view of the electrolyte key on a greatly enlarged scale.

The electrolyte key 16 projects out of the threaded nipple 27 at the other end of the metal housing 25. As FIG. 3 shows, the electrolyte key 16 has a metal jacket 48, preferably formed of zirconium, titanium, tantalum, hafnium or corrosion-resistant chrome-nickel steel. The metal jacket 48 may be tightly inserted into the metal housing 25 of the reference electrode, such as by soldering. The metal jacket 48 may also have an electrically insulating coating 49 on the outside and inside thereof which is shown at the inside only. A string 50 of asbestos fibers sheathed in a Teflon hose 51 runs inside the metal jacket 48, as a core. The asbestos string 50 communicates with the feed water of the steam generator in such a manner as to establish the electrolytic contact of the feed water with the reference electrode 15 indicated in FIG. 1.

The device illustrated in FIGS. 1 to 3 measures the corrosion potential of the tube bundle 4 and the redox potential of the steam generator feed water. If necessary, the feed water conditioning can be changed on the basis of these potentials, especially by adding hydrazine. The bandwidth provided for this control may be 100 millivolts.

The foregoing is a description corresponding in substance to German application No. P 35 04 925.1, filed Feb. 13, 1985, the International priority of which is being claimed for the instant application, and which is hereby made part of this application. Any material discrepancies between the foregoing specification and the aforementioned corresponding German application are to be resolved in favor of the latter.

We claim:

1. Method for the corrosion protection of seam generators having a housing containing feed water and enclosing a tube bundle with tubes conducting a heat carrier and being galvanically connected to the housing, which comprises continuously determining the redox potential of the feed water with a first electrode disposed inside the housing in a lower region of the tube bundle relative to a second external reference electrode outside the steam generator electrically contacting at least one tube through a electrolyte key, continuously determining the corrosion potential at least at one tube of the tube bundle by measuring the voltage of said second external reference electrode relative to the housing, and negatively shifting the redox and corrosion potentials by changing the chemicals conditioning of the feed water if the potentials indicate the danger of corrosion.

2. Method according to claim 1, which comprises adding conditioning substances dissolved in liquid to the feed water by remote control.

3. Method according to claim 2, which comprises presetting the quantity of the conditioning substances with a timing control circuit.

4. Method according to claim 1, which comprises forming the external reference electrode of a material being inert relative to the feed water.

5. Method according to claim 1, which comprises measuring the redox potential in the vicinity of a tube sheet at the bottom of the tube bundle.

6. In combination: a steam generator having a housing containing feed water to be chemically conditioned, and a tube bundle disposed in said housing, said tube bundle including tubes conducting a heat carrier and having a galvanic connection to said housing; and a device for protecting the steam generator against corrosion, the device comprising a first electrode inside the housing in a lower region of the tube bundle, a second external reference electrode disposed outside the steam generator, an electrolyte key electrolytically connecting said second external reference electrode to one of said tubes, means for continuously determining the redox potential of the feed water with said first electrode relative to said second external reference electrode, and means for continuously determining the corrosion potential of said one tube by measuring the voltage of sadi second external reference electrode relative to said housing, said electrolyte key being a tube with an outer metal jacekt, an insulating inner metal oxide coating, a thermolastic hose disposed inside said coating, and a fiber core disposed inside said hose.

7. Device according to claim 6, wherein said metal jacket is formed of a material from the group consisting of zirconium, titaniium, tantalum, hafnium and corrosion-resistant CrNi steel.

8. Device according to claim 4, wherein said fiber core is formed of asbestos and said hose is formed of polytetrafluorethylene.

9. Device according to claim 8, wherein said second external reference electrode is a second type electrode.

10. Device according to claim 8, wherein said second external reference electrode is formed of silver/silver chloride and is enclosed in a metal electrode housing.

11. Device according to claim 10, wherein said electrode housing has a threaded nipple enclosing said electrolyte key and being fastened to said steam generator housing.

12. In combination: a steam generator having a housing containing feed water to be chemically conditioned, and a tube bundle disposed in said housing, a tube sheet supporting said tube bundle including tubes conducting a heat carrier and having a galvanic connection to said tube sheet; and a device for protecting the steam generator against corrosion, the device comprising a first electrode disposed inside the housing in a lower region of the tube bundle, a second external reference electrode disposed outside the steam generator, an electrolyte key electrolytically connecting said second external reference electrode to one of said tubes, means for continuously determining the redox potential of the feed water with said first electrode relative to said second external reference electrode, and means for continuously determining the corrosion potential of said one tube by measuring the voltage of said second external reference electrode relative to said tube sheet, said electrolyte key being a tube with an outer metal jacket, an insulating inner metal oxide coating, a thermoplastic hose disposed inside said coating, and a fiber core disposed inside said hose.

13. Device according to claim 12, wherein said metal jacket is formed of a material from the group consisting of zirconium, titanium, tantalum, haflnium and corrosion-resistant CrNi steel.

14. Device according to claim 12, wherein said fiber core is formed of asbestos and said hose is formed of polytetrafluorethylene.

15. Device according to claim 9, wherein said second external reference electrode is a second type electrode.

16. Device according to claim 9, wherein said second external reference electrode is formed of silver/silver chloride and is enclosed in a metal electrode housing.

17. Device according to claim 16, wherein said electrode housing has a threaded nipple enclosing said electrolyte key and being fastened to said steam generator housing.

18. Method for the corrosion protection of steam generators having a housing containing feed water and enclosing a tube bundle with tubes conducting a heat carrier and being supported in and galvanically connected to a tube sheet, which comprises continuously determining the redox potential of the feed water with a first electrode disposed inside said housing in a lower region of the tube bundle relative to a second external reference electrode which is disposed outside the steam generator and which electrically contacts at least one tube through an electrolyte key, and continuously determining the corrosion potential at least at one tube of the tube bundle by measuring the voltage of the second external reference electrode relative to the tube sheet.

* * * * *